United States Patent
Gasser et al.

(10) Patent No.: US 10,713,554 B2
(45) Date of Patent: Jul. 14, 2020

(54) SENSOR ARRANGEMENT WITH RFID

(71) Applicant: SFS intec Holding AG, Heerbrugg (CH)

(72) Inventors: Daniel Gasser, Diepoldsau (CH); Kurt Blum, Koblach (AT)

(73) Assignee: SFS intec Holding AG, Heerbrugg (CH)

(*) Notice: Subject to any disclaimer, the term of this patent is extended or adjusted under 35 U.S.C. 154(b) by 122 days.

(21) Appl. No.: 15/901,224

(22) Filed: Feb. 21, 2018

(65) Prior Publication Data

US 2018/0240004 A1 Aug. 23, 2018

(30) Foreign Application Priority Data

Feb. 22, 2017 (EP) .................... 17157462

(51) Int. Cl.
| | |
|---|---|
| *G06K 19/077* | (2006.01) |
| *G01D 11/24* | (2006.01) |
| *E04B 1/76* | (2006.01) |
| *F16B 13/12* | (2006.01) |
| *F16B 13/00* | (2006.01) |

(52) U.S. Cl.
CPC ...... *G06K 19/07773* (2013.01); *E04B 1/7633* (2013.01); *G01D 11/245* (2013.01); *F16B 13/00* (2013.01); *F16B 13/124* (2013.01)

(58) Field of Classification Search
CPC .......... G06K 19/07773; G06K 19/0717; E04B 1/7633; G01D 11/245; F16B 13/00; F16B 13/124
See application file for complete search history.

(56) References Cited

U.S. PATENT DOCUMENTS

| | | | |
|---|---|---|---|
| 6,709,214 B1 * | 3/2004 | Angehrn | E04D 3/3603 411/533 |
| 2010/0050778 A1 * | 3/2010 | Herley | G01L 5/246 73/761 |

FOREIGN PATENT DOCUMENTS

| | | |
|---|---|---|
| JP | 2015215226 | 12/2015 |
| KR | 1020070092374 | 9/2007 |
| WO | 0068581 | 11/2000 |

* cited by examiner

*Primary Examiner* — Xin Y Zhong
(74) *Attorney, Agent, or Firm* — Volpe and Koenig, P.C.

(57) ABSTRACT

A grommet (20, 30) as part of a fastening element for a building envelope essentially comprises a head (21), a tip (22) and a sleeve (23) therebetween, wherein the head (21) is essentially constructed as an extensive washer (24), the central hole of which is adjoined by the tubular sleeve (23). The tip (22) narrows essentially in a conical or tapered manner to a smaller diameter. The grommet (20, 30) has a sensor arrangement (25), with at least one RFID transponder with antenna and a sensor operatively connected to the transponder.

6 Claims, 4 Drawing Sheets

SENSOR ARRANGEMENT WITH RFID

INCORPORATION BY REFERENCE

The following documents are incorporated herein by reference as if fully set forth: European Patent Application No. 17157462.7, filed Feb. 22, 2017.

FIELD OF THE INVENTION

The present invention is concerned with a sensor arrangement in building envelopes, particularly for measuring environmental parameters and detecting building damage.

BACKGROUND

In construction, highly complex building envelopes are used increasingly, which consist of multi-layered, functionally adapted layers. In this case, both in the outer wall and roof structures, combinations of thermal insulation layers, supporting/fixing elements, and protective membranes against environmental influences such as wind, rain, snow, etc. are used. Combinations of mineral fibre products, foams, plastic films and punctiform fastening elements therefor are conventional today in the case of roof structures specifically.

Keeping such building envelopes permanently steam- and water-tight requires not only a coordinated selection of products, but also a high degree of care during the processing and mounting. In the case of industrial roofs of sometimes thousands of square metres, where there may be hundreds of metres of weld seams between plastic film webs, the requirements are particularly high. To compound matters, the increasingly thick insulation layers can accommodate water, depending on the material, which leads to it only being possible to discover any leaks late and then the resultant damage being particularly high.

PRIOR ART

Various solutions have been described in the prior art for this problem. On the one hand, detection methods are used for leaks, which are based on various diagnostic methods. There are electrical methods, in which leak currents can be measured by a mesh of wires attached in the substructure, as soon as the electrical insulation effect of the roof structure changes due to a local penetration of water. Alternatively, tightness measurements may take place with overpressure or else imaging thermography if a thermal bridge is created by the leak. A high outlay during use or during installation is common to all of these known methods.

Methods have also already been described, which operate with the aid of RFID-coupled sensors. RFID (radio-frequency identification) systems use a semiconductor component termed a transponder, with an antenna and a reading device fitting the same. Such RFID systems have the advantage that not only the identification of the transponder takes place via the antenna, but rather also the power supply via magnetic alternating fields or by high-frequency radio pulses (induction). This power supply is also sufficient in order to operate simple sensors, e.g. moisture sensors or temperature sensors. Combined with non-volatile memories measuring networks can be built in this manner, which can get by without cabling and its own power supply.

The disadvantage of this solution is that these sensors with RFID transponder have to be laid separately, e.g. below or between various layers of the building envelope. Also, a defined installation position or installation depth (relatively e.g. to the surface of a roof surface) must be ensured—on the one hand in order to allow a comparability of the measurement results but also due to the reachability of the sensor itself.

SUMMARY

The present invention is concerned with this problem and suggests an inventive solution using one or more features of the invention. Further variants and development stages of the invention are described below and in the claims.

In building technology, fastening elements have been known for a long time, in which a combination of a plastic grommet and a screw element is used, in order to fasten a roof insulation web on a fixed substructure. EP 1 175 567 A (similar to FIG. 1) shows a grommet 10, which essentially consists of a head 11 with an extensive washer 14, the central hole of which is adjoined by a tubular sleeve 13, which narrows in a conical manner to a smaller diameter at the end remote from the head. The sleeve can accommodate a screw (not shown in FIG. 1), the shank of which can pass through the cone through an axial opening 16, the head of which stops against the cone taper 15 however. By choosing sleeves or grommets of various lengths, roof insulation webs of various thicknesses can be fixed using one screw type or length.

As is known, these grommets can be realized differently, both as regards the length of the sleeve 13 and the size and material of the extensive washer 14. Thus, it is known to manufacture the sleeve 13 and the washer 14 separately. Thus, sleeves 13 of differing length and washers 14 of different diameter and shape (polygonal, round, oval, . . . ) can be combined, which increases the use options. In addition, it is known to manufacture the washers 14 e.g. from embossed/stamped steel sheet or from plastic. Then, generally, the sleeve 13 is designed in such a manner that at the edge thereof, facing away from the tip, the sleeve has a collar, a circumferential, radially protruding edge, which acts as a stop for a washer 14 pushed on from the tip. There may also be elements which hold the same washer in its place in a detachable or permanently fixed manner, such as latching elements, clamps, adhesive bonds, etc. When "grommet" is mentioned in the following, the most basic embodiment is meant. "Grommet with extensive washer" therefore includes both the one- and the two-piece design.

The invention includes providing a fastening element of the type mentioned with an RFID transponder and a sensor system. As a result—without providing an additional processing step—it is possible to introduce a sensor in a layer of a roof structure at a defined position and depth. Likewise, additional damage to the insulation layers or the roof membrane can be prevented—the fastening point, which is present already, is used. Furthermore, it also makes things easier that, in the sector, the know-how for laying such grommet/screw systems is available and retraining or a changeover to the new system can conceivably take place easily. In addition, the planning may be facilitated. Such fastening elements are already installed in large numbers per square metre on roof areas which are highly loaded (e.g. by wind or alternate loading). The number of measurement points on such surfaces can therefore be increased (for reasons of redundancy or safety) without great planning outlay.

Wherever a fastening point with sensor element appears to not be necessary, fastening elements (grommet/screw) according to the prior art can be used, without changing the setting process itself. The "intelligent" RFID setting points can be differentiated from the normal fastening points by means of different coloured labelling. If magazine strips are used, in which the fastening elements are inserted into a setting device in a bundled manner, the number or the ratio of "intelligent" to normal fastening elements can be set and thus an error during mounting can be prevented from the start.

In essence, a grommet 20, 30 essentially includes a head 21, a tip 22 and a sleeve 23 therebetween, wherein the head 21 can be constructed as a washer 24 (which is extensive, detachable or fixed, depending on the use case) or as a stop collar 17. The external shape of the washer 24 can (preferably) be realized to be circular, furthermore oval or polygonal with and without edge rounding. The tubular sleeve 23, which in turn opens into the tip 22, adjoins the head 21. This tip can preferably essentially have a conical (26) or tapered shape 27 and therefore narrows to a smaller diameter than the sleeve 23. According to the invention, the grommet 20, 30 will have a sensor arrangement 25, with at least one RFID transponder with antenna and a sensor operatively connected to the transponder.

These grommets can, like those known in the prior art, be produced as an injection moulded part made from plastic. The sensor arrangement can in this case be inserted into the mould before the injection moulding process and thus completely or partially surrounded by the plastic of the grommet. Alternatively, a subsequent fastening or attachment of the sensor arrangement on the grommet is also possible. As in the prior art, the sleeve element with the tip and the washer can be manufactured separately and connected by plugging together (in a detachable manner or in a non-detachable manner e.g. by latching or clamping or adhesive elements) prior to mounting.

In a preferred embodiment, the grommet 20, 30 is characterized in that the sensor arrangement 25 is attached flat on the outer side of the sleeve 23, on the washer 24 or on the tip 22. As a result, the sensor, like the antenna of the transponder, can be seen from the outside and the measurement takes place in direct contact with the surrounding material.

Depending on the arrangement profile, it may be advantageous to arrange the sensor arrangement on the grommet 32 in a spatially distributed manner on or at the grommet 32. Here, spatially distributed means a certain spatial separation of the measuring sensor (sensor) 25a itself from the transponder 25b with antenna. In a preferred variant, the transponder 25b with antenna is located close to the head on the sleeve 23 or on the washer 24 itself, whilst the sensor 25a is attached close to the tip on the sleeve 23 or on the tip 22 itself. As a result, e.g. during temperature measurements, the measurement points can be attached a defined depth of the insulation layer, whilst the antenna itself lies closer to the surface of the building envelope, which improves the reception and transmission conditions. As the grommets should all assume the most identical installation positions possible during installation, all sensors are also located at the same depth, which enormously facilitates the comparability of resultant measurement results over a roof surface.

Depending on the design, it may also be advantageous to provide a grommet 20, 30 with a sensor arrangement 25, which is attached in a detachable manner. Here, the advantage lies in the flexibility of the arrangement of the sensor system, if required.

Alternatively and somewhat preferably, the sensor arrangement 25 is connected to the grommet in a non-detachable manner. The sensor arrangement can be glued on, tacked on, welded on, embedded or integrated into the grommet at least to some extent as part of the production process. Gluing on or tacking on make sense if the sensor arrangements are present as a separate thin-layer component on an adhesive film or are provided for welding on. It is likewise conceivable to attach the components, the antenna and/or the conductor tracks in a printing method, e.g. by a transfer printing method. This would primarily have considerable advantages in the case of non-planar substrates.

In a variant according to the invention, a grommet 20 will have a through opening 28 at or in the tip 22, coaxial to the central axis 29 of the sleeve 23. This through opening is used to pass through a fastener 41, which can be introduced into the grommet at the head side with the tip at the front. The fastening on a building envelope subsequently takes place as is known from the prior art. In this case, the grommet 20 is supplemented by the fastener 41 to form a fastening element 40, using which insulation layers 42 can be fastened on a fixed substructure 43. Depending on the use profile or design, the fastener 41 may, as part of the fastening element 40, be a wood screw, a sheet metal screw, a concrete screw, a bolt or a rivet.

In the sense of the invention, a grommet comprises both variants with and without through opening 28. So it would be conceivable and advantageous to insert a grommet purely as a pluggable element into a roof web or insulation layer, even without using the grommet with a fastener 41 as fastening element 44 (cf. FIG. 4) ("plug-in grommet"). The advantages of the accurate-depth attachment are retained, likewise the customary mounting together with other fastening elements 40. Thus, a grommet 44 can have a tip, as shown in FIG. 2 on the left, which tip facilitates the penetration of the insulation material 42.

In context, the sensor arrangement 25 is also considered as part of the invention, comprising an RFID transponder with antenna and at least one sensor operatively connected to the transponder. The sensor arrangement is designed to be used as part of a fastening element 40, which in turn can be used as part of a fastening system 45 for a building envelope.

Even if the description does not directly express all possible combinations of the features, the combinability of such features is not excluded thereby.

DETAILED DESCRIPTION OF THE PREFERRED EMBODIMENTS

Figure 1:
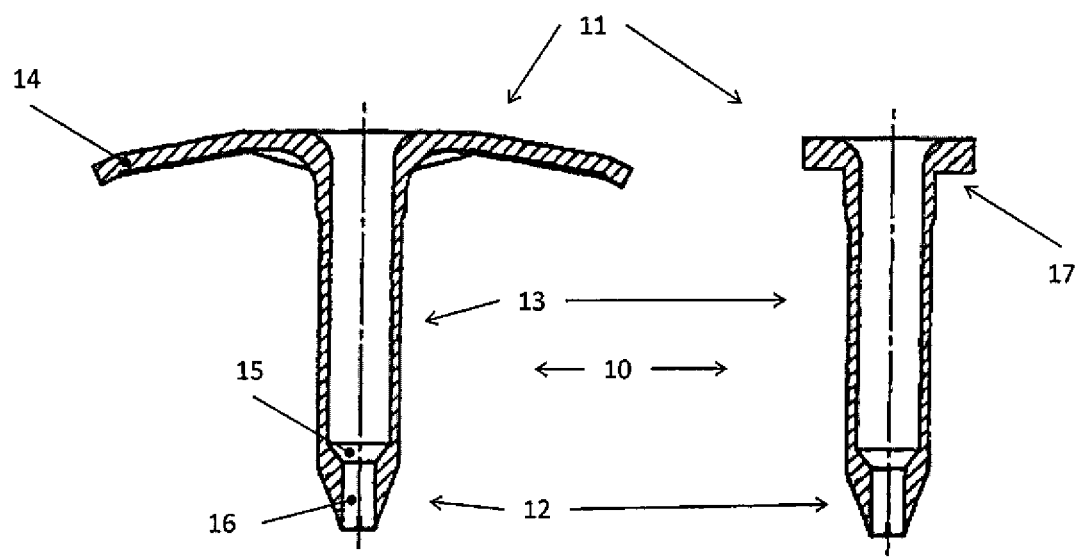
FIG. 1 is a cross-sectional view through two prior art fastening elements.
Figure 4:
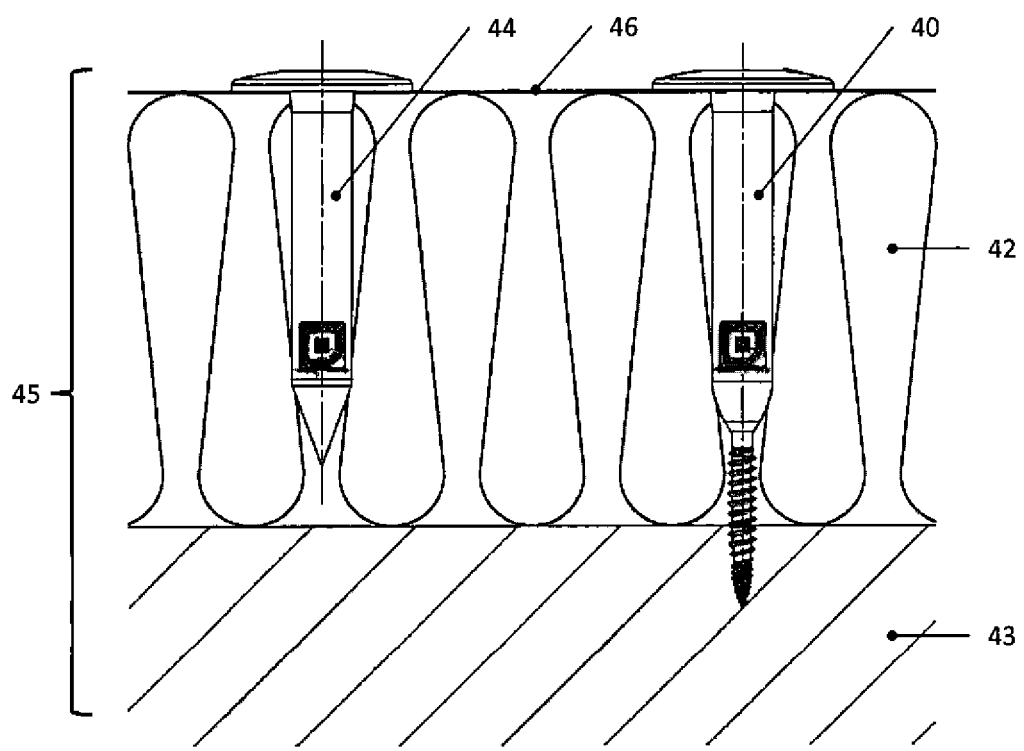
FIG. 4 shows a fastening system installed with a fastening grommet with a fastener as well as a plug-in grommet.

FIG. 1 shows a fastening element 10 according to the prior art in two variants. In the design on the left, the head 11 is constructed as an extensive washer 14, which, as shown in FIG. 4, can bear against an insulation layer of a roof covering and then distribute the vertical tensile forces. The variant in FIG. 1 on the right only has a stop collar 17, which can be combined with various washers. A tubular sleeve 13 connects the head 11 to a conical tip 12 in each case, as shown in section. The sleeve narrows in the cone in feature 15 and merges into an axial opening 16.

Figure 2:
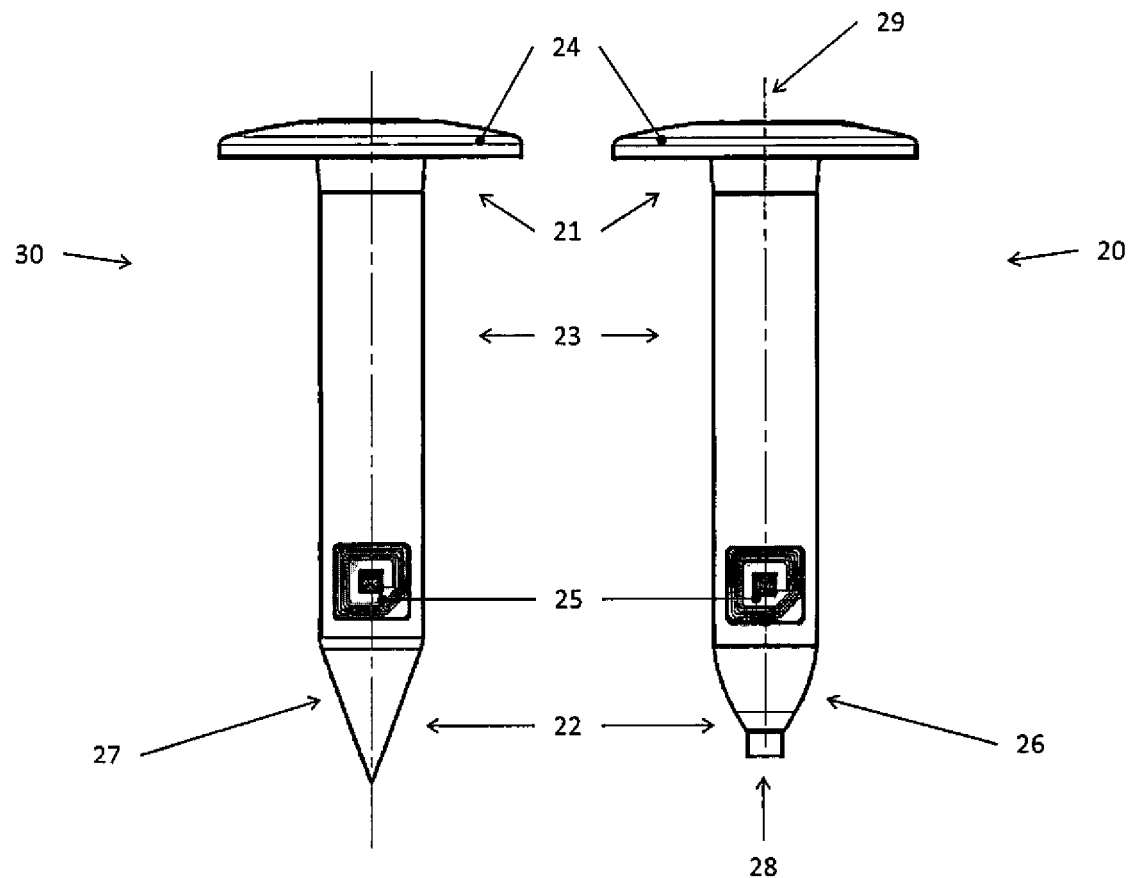
FIG. 2 shows two embodiments of fastening grommets according to the invention.
Figure 3:
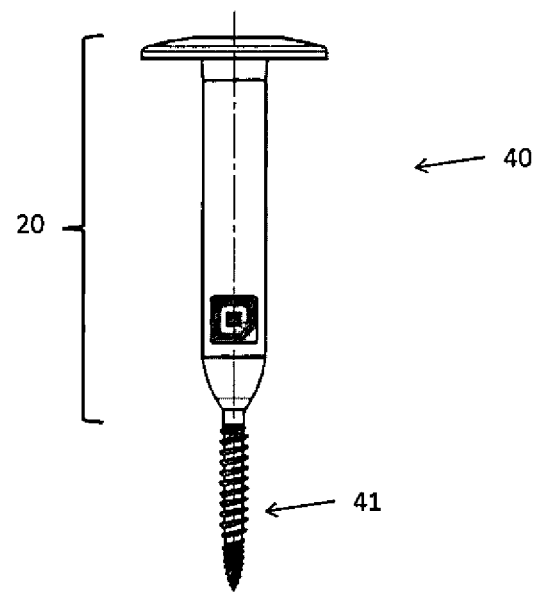
FIG. 3 shows an embodiment of a fastening grommet with a fastener installed therein.

FIG. 2 shows the two preferred main variants of the grommet according to the invention. The variant in FIG. 2 on the right corresponds to a grommet 20, the purpose of which includes the function as part of a fastening element, as illustrated in FIG. 4 ("fastening grommet"). The variant of a grommet 30, on the left in the image, corresponds to the pure plug-in element without fastening function ("plug-in grommet"). The design made up of head 21 with washer 24, sleeve 23 and tip 22 essentially corresponds to that of FIG. 1 and is comparable for grommet 20 and 30. The shape of the tip 22 is determined technically and is designed by the person skilled in the art, taking account of manufacturing specifications, as required by the intended use. A closed tip is recommended for the plug-in grommet 30 with tip 27. The fastening grommet 20 has the through opening 28 at the tip, in order to accommodate a fastener 41, as shown in FIG. 3 or FIG. 4. This opening is coaxial to the central axis 29 of the sleeve 23. The attachment of the sensor arrangement 25 is shown by way of example, but illustrates that both the fastening grommet and the plug-in grommet allow the same installation position and depth.

FIG. 3 shows the combination of a fastening grommet 20 with a plugged-in fastener 41 as fastening element 40.

FIG. 4 shows a fastening system 45 with a fixed substructure 43, an insulation layer 42 arranged thereon and a cover film 46. The fastener 41 of a fastening element 40 is anchored in the substructure 43, whilst the plug-in grommet 48 manages without a fastener. The installation depth of the sensor arrangement is the same. This is not a compulsory feature, cross-sectional measurements of a chosen parameter (temperature, moisture, . . . ) can readily be achieved over the layer 42 by means of the different arrangement of the same sensor types.

Figure 6:
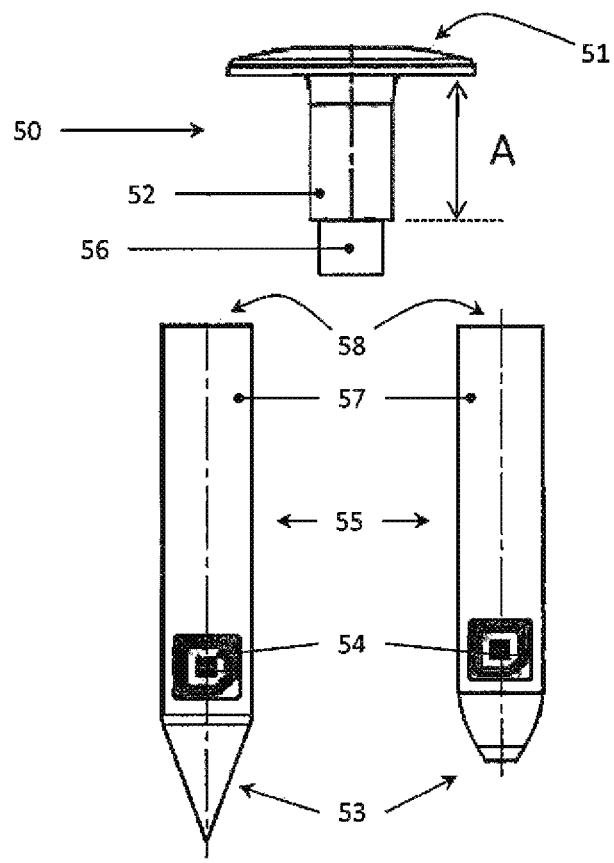
FIG. 6 shows two additional embodiments of the plug-in grommet shown in FIG. 2, with different tip shapes and lengths.

FIG. 6 shows two variants of the above-described "plug-in grommet" 30 shown in FIG. 2, with different tip shapes and lengths. One special feature here is the design in two parts. An upper part 50 consists primarily of a head 51 and a rod-shaped body 52. This optionally has an adapter 56 at the end facing away from the head 51, which adapter may correspond to a counterpart piece on a sensor carrier 55. The adapter may be a cone, a cylinder, a square or a polygon. The counterpart piece, a receptacle 58, is correspondingly shaped in such a manner that it can be connected in a non-positive- or positive-fitting manner. The placement of adapter 56 and receptacle 58 can of course also be reversed.

The head 51 can, as shown, be realized in a disc-shaped manner, but could in turn also have a specifically shaped point of action for a (manual or motorized) tool or a coupling or an interface for a rotary or striking tool. The length A in FIG. 6 determines the embedded depth of the sensor carrier 55 in the design shown. The upper part 50 as a whole therefore essentially fulfils the task of a setting tool (applicator) for the sensor carrier 55.

Figure 5:
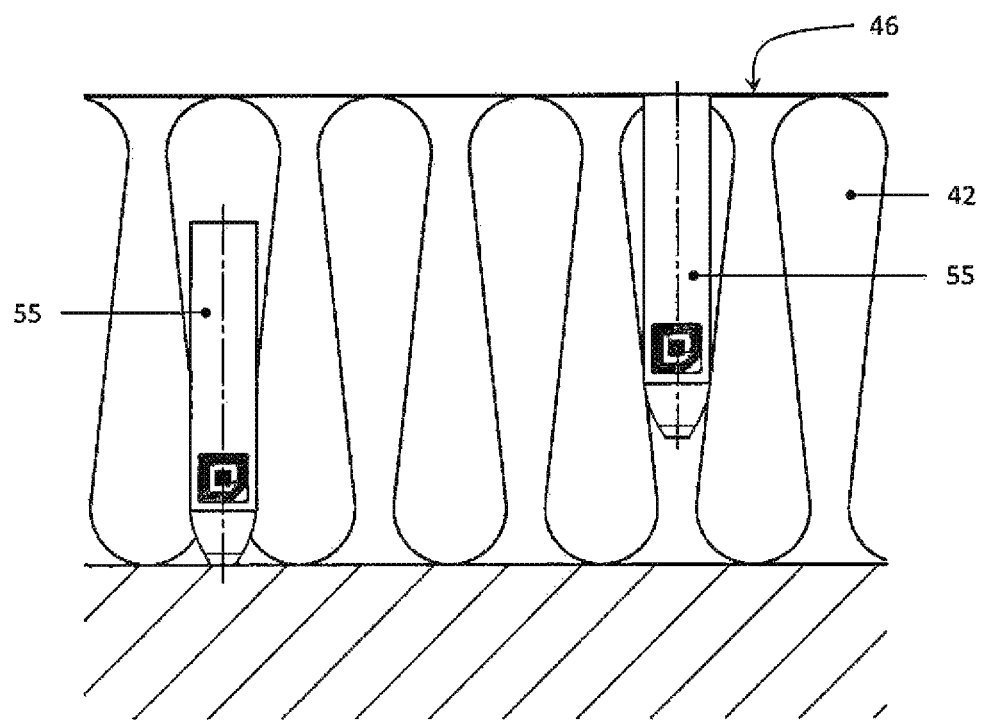
FIG. 5 shows sensor carriers according to a further embodiment installed at different positions.

The sensor carrier 55 itself consists of a rod-shaped body 57, on or in which a sensor arrangement 54 is attached. The options for attachment (placement and type) here also analogously include that already mentioned above. A tip 53 is located at one end of the body 57, the receptacle 58 is located at the other end. The sensor carrier 55 is plugged or driven, with the tip 53 at the front, into the insulation layers 42 of the roof structure. FIG. 5 shows the installation situation here. The body of the sensor carrier 55 can in this case follow the dimensions and materials of those described for the grommet, that is only preferred however and not compulsory. The rod-shaped body 57 can have a round, circular, polygonal/angular or square cross section and can be produced as a hollow body or solid body. A mixture is also conceivable, e.g. with a solid tip and a sleeve-shaped longitudinal body 57. The above-described receptacle 58 is preferred, because it allows a controlled and plannable attachment or introduction of the sensor body (check of angle and penetration depth). However, if the sensor carrier should only be plugged in flush with the surface, as shown on the right in FIG. 5, then under certain circumstances it is possible to dispense with the use of a tool and then the use of the upper part would be omitted and also a special receptacle 58 would not be necessary.

In the simplest design, a sensor carrier 55 therefore comprises a rod-shaped solid and/or hollow body 57 with a round, circular, polygonal/angular or square cross section, on or in which a sensor arrangement 54 is attached. As described above, this comprises an RFID transponder and a sensor. A tip 53 is located at one end of the rod-shaped body, a receptacle can be located at the other end, which receptacle can interact in a positive and/or non-positive manner with an adapter 56 of an upper part 50. The upper part 50 acts as a tool for introducing the sensor carrier and has a head 51, which can have a tool receptacle and/or a disc-shaped shape.

Figure 7:
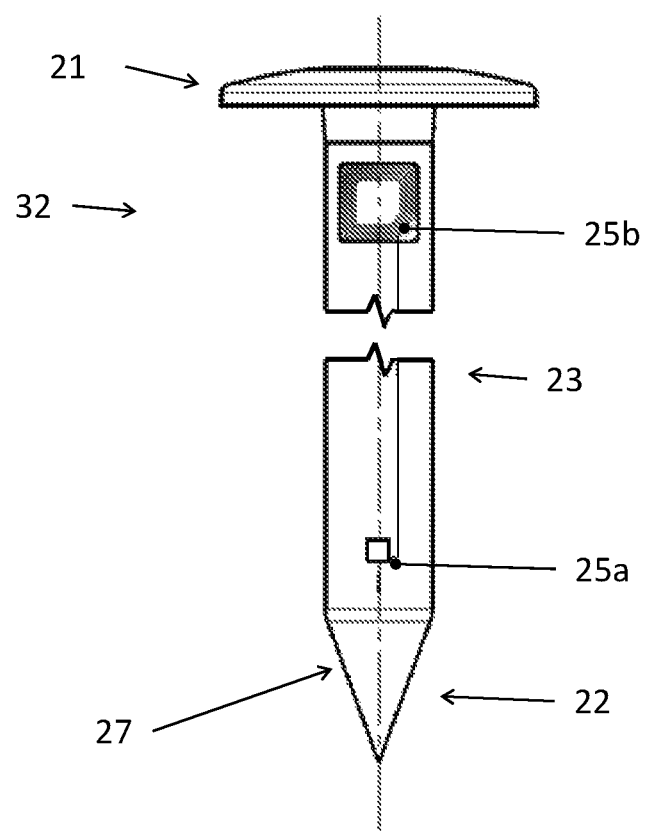
FIG. 7 is view of a screw similar to FIG. 2 of a plug-in grommet with a spatial separation of the schematically represented measuring sensor itself from the transponder with antenna, with the transponder with antenna being located close to the head on the sleeve and the sensor attached close to the tip on the sleeve.

FIG. 7 shows a combined grommet and sensor arrangement 32 designed as plug in grommet similar to the embodiment 30 in FIG. 2. In place of the combined sensor arrangement 25 of FIG. 2 with the commonly located sensor and transponder with the antenna, the sensor 25a, shown schematically, has been configured to be spatially distributed from the transponder 25b, with both being arranged in a flat manner on the outer side of the sleeve with the transponder 25b being located close to the head 21 on the sleeve 23 and the sensor 25a being located close to the tip 22 (here again shown as tapered tip 27).

| LIST OF REFERENCE NUMBERS | |
|---|---|
| 10 | Grommet |
| 20 | Grommet, fastening grommet |
| 30, 48 | Grommet, plug-in grommet |
| 11 | Head |
| 12 | Tip |
| 13 | (Tubular) sleeve |
| 14 | (Extensive) washer |
| 15 | Cone taper |
| 16 | Axial opening |
| 17 | Collar, stop collar |
| 21 | Head |
| 22 | Tip |
| 23 | (Tubular) sleeve |
| 24 | Washer |
| 25 | Sensor arrangement |
| 26 | Conical tip |
| 27 | Tapered tip |
| 28 | Through opening |
| 29 | Central axis |
| 40 | Fastening element |
| 41 | Fastener |
| 42 | Insulation layer(s) |
| 43 | (Fixed) substructure |
| 44 | Grommet (without through opening 28) |
| 45 | Fastening system for building envelope |
| 46 | Cover film |
| 50 | Upper part |
| 51 | Head 51 |

-continued

LIST OF REFERENCE NUMBERS

| 52 | (Rod-shaped) body |
| 53 | Tip |
| 54 | Sensor arrangement |
| 55 | Sensor carrier |
| 56 | Adapter |
| 57 | (Rod-shaped) body |
| 58 | Receptacle |

The invention claimed is:

1. A combined grommet and sensor arrangement,
the sensor arrangement comprising:
   an RFID transponder with antenna, and
   at least one sensor operatively connected to the RFID transponder;
the grommet comprising:
   a head with a washer,
   a sleeve, and
   a tip;
the RFID transponder with antenna and the at least one sensor are arranged in a spatially distributed flat manner;
the RFID transponder with antenna is located on the sleeve or on the washer;
and the sensor is arranged on the sleeve closer to the tip than the RFID transponder or on the tip such that the sensor is introducible at a defined installation position and depth in a layer of a roof structure.

2. The arrangement according to claim 1, wherein the grommet is a plug-in element with a closed tip.

3. The arrangement according to claim 1, wherein the grommet is a fastening element with a tip including a through opening adapted to receive a fastener.

4. The arrangement according to claim 3, wherein the through opening is coaxial to a central axis of the sleeve.

5. The arrangement according to claim 1, wherein the tip of the tubular sleeve of the grommet narrows in an essentially conical or tapered manner from a sleeve diameter to a smaller diameter.

6. The arrangement according to claim 1, wherein the fastening element is adapted to fasten insulation layers on a fixed substructure.

* * * * *